(12) United States Patent
Burdinski

(10) Patent No.: US 7,687,275 B2
(45) Date of Patent: Mar. 30, 2010

(54) NITRIC OXIDE DETECTION

(75) Inventor: Dirk Burdinski, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/065,545

(22) PCT Filed: Sep. 4, 2006

(86) PCT No.: PCT/IB2006/053095

§ 371 (c)(1),
(2), (4) Date: Mar. 3, 2008

(87) PCT Pub. No.: WO2007/029164

PCT Pub. Date: Mar. 15, 2007

(65) Prior Publication Data

US 2008/0261322 A1    Oct. 23, 2008

(30) Foreign Application Priority Data

Sep. 6, 2005    (EP)    ................... 05300719

(51) Int. Cl.
*G01N 33/00*    (2006.01)
(52) U.S. Cl. .................. 436/116; 436/73; 436/110; 436/127; 436/132; 250/336.1; 250/372; 250/373; 385/12; 385/38; 385/127; 385/128
(58) Field of Classification Search ............... None
See application file for complete search history.

(56) References Cited

U.S. PATENT DOCUMENTS 3,399,965 A    9/1968    Kalous (Continued)

FOREIGN PATENT DOCUMENTS

JP    53046085 A    4/1978

(Continued)

OTHER PUBLICATIONS

Zhang, Xueji, et al. A novel microchip nitric oxide sensor with sub-nM detection limit, 2002, Electroanalysis, vol. 14(10), pp. 697-703.*

(Continued)

*Primary Examiner*—Yelena G. Gakh
*Assistant Examiner*—Robert Xu

(57) ABSTRACT

The present invention relates to a method for amplifying the detected signal in a gas sensor. More specifically, the present invention relates to a method for increasing the concentration of the gas which is being detected in a sample or increasing the concentration of a gas which is directly obtained from the gas in the sample by chemical reaction. The gas which is to be detected is nitric oxide (NO). In particular, the method concerns the selective conversion of NO to NO2 which allows a threefold amplification of the number of analyte molecules in NO trace gas analysis in a single amplification cycle. Subsequent reduction or thermal decomposition of the obtained NO2 can provide NO again, which can again be introduced in a new amplification cycle. Multiple (n) amplification cycles can provide a sensitivity amplification by a factor $3^n$. The method can be combined with a multitude of detection methods and tolerates a high humidity. The method is therefore of general use in the analysis of NO from a variety of sources.

13 Claims, 3 Drawing Sheets

U.S. PATENT DOCUMENTS

| | | | |
|---|---|---|---|
| 6,284,212 | B1 | 9/2001 | O'Brien |
| 6,612,306 | B1 | 9/2003 | Mault |
| 6,635,415 | B1 | 10/2003 | Bollinger et al. |
| 6,636,652 | B1 * | 10/2003 | Kopelman et al. ............ 385/12 |
| 6,982,426 | B1 * | 1/2006 | Lucht et al. ................. 250/373 |
| 2004/0180448 | A1 | 9/2004 | Lehmann et al. |
| 2004/0235184 | A1 | 11/2004 | Swager |
| 2005/0065446 | A1 | 3/2005 | Talton |

FOREIGN PATENT DOCUMENTS

WO      WO02088691 A2     11/2002

OTHER PUBLICATIONS

Saliba et al: "Reaction of Gaseous Nitric Oxide With Nitric Acid on Silica Surfaces in the Presence of Water at Room Temperature"; Journal of Physical Chemistry A, vol. 105, Oct. 20, 2001, pp. 10339-10346.

Polzat et al: "Determination of Nitrogen Dioxide by Visible Photoacoustic Spectroscopy"; Analytical Chemistry, American Chemical Society, vol. 54, No. 9, Aug. 1982, pp. 1485-1489.

Robinson et al: "Luminol/H2O2 Chemiluminescence Detector for the Analysis of Nitric Oxide in Exhaled Breath"; Analytical Chemistry, American Chemical Society, vol. 71, No. 22, Nov. 15, 1999, pp. 5131-5136.

Goodman et al: "Spectroscopic Study of Nitric Acid and Water Adsorption on Oxide Particles: Enhanced Nitric Acid Uptake Kinetics in the Presence of Adsorbed Water"; Journal of Physical Chemistry A, vol. 105, 2001, pp. 6443-6457.

Addison, D.: "Dinitrogen Tetroxide, Nitric Acid, and Their Mixtures as Media for Inorganic Reactions"; American Chemical Society, Chem. Rev. 1980, vol. 80, pp. 21-39.

Fruhberger et al: "Detection and Quantification of Nitric Oxide in Human Breath Using a Semiconducting Oxide Based Chemiresistive Microsensor"; Sensors and Actuators B 76, Jun. 1, 2001, pp. 226-234.

* cited by examiner

NITRIC OXIDE DETECTION

The present invention relates to a method for amplifying the detected signal in a gas sensor. More specifically, the present invention relates to a method for increasing the concentration of the gas which is being detected in a sample or increasing the concentration of a gas which is directly obtained from the gas in the sample by chemical reaction. The gas which is to be detected is nitric oxide (NO).

In particular, the method concerns the selective conversion of NO to $NO_2$ which allows a threefold amplification of the number of analyte molecules in NO trace gas analysis in a single amplification cycle. Subsequent reduction or thermal decomposition of the obtained $NO_2$ can provide NO again, which can again be introduced in a new amplification cycle. Multiple (n) amplification cycles can provide a sensitivity amplification by a factor $3^n$. The method can be combined with a multitude of detection methods and tolerates a high humidity. The method is therefore of general use in the analysis of NO from a variety of sources.

NO is a colourless, odourless, gas of low molecular weight and is not easily detectable by conventional methods. Nitric oxide is one of the most important trace gases in human exhaled breath in so far as medical testing is concerned. Exhaled breath testing allows the non-invasive analysis of important bio markers that are indicative of a variety of diseases. The method thus has a number of medical applications.

Breath testing is developing rapidly as an important area of technology. One of the advantages of this type of testing is that the tests are non-invasive and are relatively easy to perform and economic to analyse. Prime examples of breath testing are in the monitoring of asthma, the monitoring of levels of alcohol in breath, in the detection of stomach disorders, in the detection of acute organ rejection and there are also early indications that pre-screening of breast and lung cancers may also be possible. A number of disclosures such as Fruhberger et al, Sensors and Actuators B76 (2001), 226-234, describe methods of measuring nitric oxide concentrations in human breath. In that particular case, a semi-conducting metal oxide sensor is used to measure nitric oxide concentrations.

Saliba et al, J. Phys. Chem. A2001, 105, 10339-10346, describe the reaction of gaseous NO with $HNO_3$ on borosilicate glass in the presence of water. Those workers confirmed that the stoichiometry of the reaction is that two molecules of nitric acid at the surface of the substrate react with one molecule of nitric oxide to form three molecules of nitrogen dioxide and one molecule of water, with the molecule of water remaining on the surface of the substrate. Nitric acid is known to be readily taken up on a variety of surfaces such as silica.

This document investigated the relationship between the gas phase water vapour concentration and the amount of water on the surface. The authors concluded that the nitric acid readily desorbs back into the gas phase in a dry cell but that most of it remains on the surface where water is present. They concluded that in order for the reaction to proceed the nitric acid must be on the surface and that water must be present. They conclude that nitric acid is hydrogen-bonded to the surface and to a water molecule or water molecules and that this represents a stabilised arrangement relative to the gas phase.

Because nitrogen dioxide is much less soluble in water than is the intermediate nitrous acid (HONO) which is formed as an intermediate product, the intermediate nitrous acid remains on the surface to undergo a further action with the adsorbed nitric acid, thereby leading to the overall stoichiometry discussed above. The authors confirmed that the overall reaction stoichiometry as shown in equation 1 below corresponds to three molecules of nitrogen dioxide produced per molecule of nitric oxide reacted and that the reaction is first order with respect to nitric oxide.

$$NO_{(g)} + 2HNO_{3(surface)} \rightarrow NO_{2(g)} + N_2O_{4(surface)} + H_2O \rightarrow 3NO_{2(g)} + H_2O \quad (1)$$

According to equation 1, each molecule of NO reacts with 2 molecules of immobilized $HNO_3$ to form eventually three molecules of $NO_2$, which are released to the gas phase.

U.S. Pat. No. 3,399,965 discloses a method for the production of nitric acid in an existing nitric acid plant. In this process nitric acid formed at a nominal 58% strength is diverted to the production of 68 to 70% nitric acid by contacting part of the cooled burner gas from the existing plant with 68 to 70% nitric acid under conditions which oxidise the nitric oxide in the gas to higher oxides of nitrogen. The reaction involves the reaction of one molecule of nitric oxide with two molecules of nitric acid to produce three molecules of nitrogen dioxide and one molecule of water. In this process, the reaction is maintained at a temperature of about 60 to 140° F. (15 to 60° C.) and a pressure of about 80 to 150 psi.

U.S. Pat. No. 6,284,212 discloses a method for forming nitric acid using a catalytic solution. The overall stoichiometry for this process is said to involve the reaction of four molecules of nitric oxide with three molecules of oxygen and two molecules of water to form four molecules of nitric acid. In that disclosure, the process aims to suppress the nitric oxide gas effluence from an aqueous solution and intends to provide a means for oxidising nitric oxide to higher oxides of nitrogen without relying on non-homogeneous gas phase oxidation.

None of the prior art documents discloses a method for handling and analysing a sample of exhaled air for nitric oxide content.

One problem with measuring exhaled nitric oxide is that it occurs in exhaled breath at the level only of parts per billion (ppb) and as such, can only be measured using bulky and expensive spectroscopic equipment. There is therefore a need for a system which will enable the detection of very low levels of nitric oxide in a gaseous sample. There is also a need for a system which is relatively easy to operate and inexpensive. The system should be capable of amplifying the number of molecules of a trace amount of gas in a sample by at least three times. There is thus a need for a system which allows the number of molecules of nitric oxide to be increased relative to the amounts of the other components in an exhaled breath sample.

We have found that it is possible to increase the detected signal attributable to the nitric oxide in an exhaled breath sample by selective chemical transformation of the nitric oxide component to a product which is formed directly from nitric oxide and which itself is easily capable of detection and analysis by conventional techniques. The present invention satisfies some or all of these aims.

According to a first aspect of the present invention, there is provided a method of determining the concentration of nitric oxide in a gaseous sample, wherein the method comprises the following steps:

a) collecting a gaseous sample containing nitric oxide,
b) exposing the sample to a first substrate to which nitric acid is bound in the presence of water to form nitrogen dioxide by oxidation of the nitric oxide, and
c) determining) the concentration of nitric oxide in the gaseous sample from the nitrogen dioxide produced in step (b).

The present invention therefore provides a method of amplifying the detected signal attributable to nitric oxide in a gaseous sample, such as a breath sample. The gaseous sample of known volume may be collected under ambient conditions of pressure and temperature and the conditions of pressure and temperature are known. The temperature of the sample may be measured by any conventional means. The concentration of the nitrogen dioxide produced after the oxidation step can be measured and the measured concentration of the nitrogen dioxide will be three times that of the original nitric oxide used as the starting material in the oxidation process. This is due to the stoichiometry of the reaction used in the method.

Alternatively, the nitrogen dioxide may be reduced to nitric oxide whose concentration may then be measured. The measured concentration of the nitric oxide will be the same as that of the original nitrogen dioxide used as the starting material in the reduction process due to the stoichiometry of the reaction used in the method.

Where further chemical amplification is needed, the method will comprise a number of sequential reduction and oxidation steps which follow the initial oxidation step i.e. these sequential reduction and oxidation steps will follow the oxidation performed in step (c) described above. In each oxidation step used, oxidation is achieved by exposing the nitric oxide to a substrate to which nitric acid is bound in the presence of water to form nitrogen dioxide.

The reducing agent may be the same or different in each reducing step used. Preferably, it will be the same in each case.

The reduction and oxidation steps can be repeated as many times as is required. The final step may be either an oxidation or a reduction. Preferably, the final step is an oxidation with the result that the species whose concentration to be measured is nitrogen dioxide.

In a preferred embodiment, the measurement of the concentration of nitric oxide or of the concentration of nitrogen dioxide is non-invasive in the sense that it does not consume any material. This is achieved by spectroscopic measurement of the gas concentration. measurement can also be made by conventional gas chromatographic methods. Thus in addition to taking a final measurement of the gas concentration after the final reaction step, the concentration of either nitrogen dioxide or of nitric oxide can also be measured after one or more intermediate steps in the overall method without disturbing the overall process.

In an embodiment, the gaseous sample is a sample of breath.

In another embodiment, the concentration of nitric oxide or nitrogen dioxide is measured by spectroscopy.

In an embodiment, the chemical scrubbing unit is an acidic or neutral column through which the sample gas is initially passed before the amplification process. Preferably the scrubbing unit is an acidic ion exchange column.

In another aspect of the invention, discussed in more detail later, the reaction chambers containing the oxidising agent (nitric acid and water) and the reducing agent need not be separate vessels and both reactions can be carried out in a single chamber. The reactions are effectively performed at the same time. In this case, the nitric acid and water are immobilized on or within a suitable substrate and the reducing agent is also immobilized on or within a different substrate formed of similar or the same material. The two substrates are present in the same vessel which is the reaction chamber. The substrates may be mixed intimately or may be mixed so as to form discrete layers or other similar arrangements. The column may be considered to be a composite column in this case as it contains all the materials necessary for both the oxidation and the reduction reactions to take place in a single reaction zone. In this case, in a further embodiment, the composite column could be combined with a subsequent separate oxidation or reduction step prior to gas detection, depending on which gas is to be analysed (oxidation for $NO_2$ detection, reduction for NO detection).

The detected signal attributable to the nitric oxide in an exhaled breath sample can be increased by selective chemical transformation of the nitric oxide component to a product which is formed directly by chemical transformation in one or more steps starting from the nitric oxide in the sample. The product formed from the original nitric oxide is itself easily capable of detection and analysis by conventional techniques. One such product is nitrogen dioxide and this is produced in an amount corresponding to three times the amount of the original nitric oxide. The stoichiometry of this reaction means that three moles of nitrogen dioxide are formed from one mole of nitric oxide. Measurement of the concentration may then be performed on the nitrogen dioxide itself. In principle, the total concentration of detectable molecules is thus increased selectively by a factor of 3, while, in this first instance, the species to be detected becomes $NO_2$ instead of NO. The option to re-reduce $NO_2$ to NO is discussed below.

We have also found that it is possible to react the product of the first amplification step itself, for example nitrogen dioxide, to form another product which is also easily capable of detection and analysis by conventional techniques. We have thus found that the nitrogen dioxide produced in the first amplification step may be reacted to form nitric oxide. The nitric oxide is reformed in an amount corresponding exactly to the amount of the nitrogen dioxide produced in the first amplification step. The stoichiometry of this reaction means one mole of nitric oxide is formed from one mole of nitrogen dioxide. The amount of nitric oxide thus formed could be measured at this stage if desired.

However, more preferably, the nitric oxide is reacted further in a second amplification step to form a further product which is also easily capable of detection and analysis by conventional techniques. This further product is preferably also nitrogen dioxide, with the result that a further three-fold increase in the concentration is achieved relative to the concentration of the nitrogen dioxide formed in the first amplification step or the nitric oxide reformed after the first amplification step. The concentration of the nitrogen dioxide can then be measured. The net effect after the two amplification steps is a 9-fold (i.e $3^2$) amplification in the amount of the desired species or a species derived directly from it by one or more chemical transformation steps. Equally, the nitrogen dioxide formed at this stage could be reacted further to form nitric oxide.

The process is summarised in the Scheme 1 below:

$$x\,NO + 2x\,HNO_3 \longrightarrow 3x\,NO_2 + x\,H_2O \quad (2.1a)$$

$$3x\,NO_2 + 3x\,[Red] \longrightarrow 3x\,NO + 3x\,[Red]O \quad (2.1b)$$

$$3x\,NO + 6x\,HNO_3 \longrightarrow 9x\,NO_2 + 3x\,H_2O \quad (2.2a)$$

$$9x\,NO_2 + 9x\,[Red] \longrightarrow 9x\,NO + 9x\,[Red]O \quad (2.2b)$$

$$\ldots\ldots\ldots\ldots\ldots\ldots\ldots\ldots\ldots\ldots\ldots\ldots\ldots\ldots \quad (2.\text{na})$$

$$\ldots\ldots\ldots\ldots\ldots\ldots\ldots\ldots\ldots\ldots\ldots\ldots\ldots\ldots \quad (2.\text{nb})$$

$$\text{NO} \text{---[n-cycles]} \longrightarrow 3^n\,\text{NO} \quad (3)$$

The re-reduced NO can subsequently be fed back into another amplification cycle (equations 2.n). In principle, after n cycles $3^n$ molecules of NO are obtained for each molecule of NO fed into the system, which corresponds to a sensitivity increase by a factor of $3^n$ (equation 3; e.g. 4 cycles would already allow for a sensitivity improvement by a factor of 81). Thus 4-5 cycles allow for an amplification from the usual breath concentrations of some 10 ppb to the more easily detectable ppm range. The amplification can be achieved reliably and repeatably. The method is universally applicable, since it can be combined with NO detection methods based the analysis of NO as well as $NO_2$.

The present invention also relates to an apparatus for measuring the concentration of nitric oxide in a gaseous sample.

According to another aspect of the present invention, there is provided an apparatus for measuring the concentration of nitric oxide in a gaseous sample, the apparatus including the following components arranged in fluid communication:

a first vessel for collecting a gaseous sample containing nitric oxide;

a first reaction chamber in fluid communication with the first vessel containing a first substrate whose surface is able to provide a source of nitric acid and water enabling the formation of nitrogen dioxide after exposition of the sample to the first substrate; and, means for determining the concentration of the nitric oxide from the nitrogen dioxide In an embodiment, the first gaseous product may be reacted to form a second gaseous product in a reduction reaction. This takes place in a second reaction chamber which contains a reducing agent. The reducing agent may be held on a substrate or may be present on its own in the chamber.

The second chamber is in fluid communication with the first chamber. The nitrogen dioxide produced in the first chamber is fed to the second chamber for reduction to nitric oxide. In an embodiment, the second chamber is in fluid communication with means for measuring the concentration of gas produced therein. The concentration of the nitric oxide may then be measured by the measurement means which is in fluid communication with the second chamber. Preferably this is a spectrometer or conventional gas chromatographic equipment. Alternatively, a detector based on a field effect transistor (either an organic or an inorganic FET) could be used to measure the concentration of the gas.

If the nitric oxide which is formed in the reduction step is to be further amplified in another reaction step, the second chamber is then in fluid communication with a further chamber containing a substrate whose surface bears nitric acid and water. This may be a third reaction chamber. In an embodiment, this further chamber may be the first chamber. In this embodiment, suitable pipework, and any necessary flow valves etc, provide fluid communication back to the first reaction chamber and the oxidation step is repeated there. The concentration of the resulting nitrogen dioxide may be measured at this point. In an embodiment, in either case when the measurement means which is in fluid communication with the second chamber is present valves or other control means can be provided to prevent the nitric oxide entering instead of completing a further reaction cycle.

Alternatively, or in addition, the resulting nitrogen dioxide produced in the further reaction chamber may be fed to another chamber containing a reducing agent to undergo reduction to nitric oxide. This may be a fourth reaction chamber. In an embodiment, the fourth (another) chamber may be the second chamber. In this embodiment, suitable pipework, and any necessary flow valves etc, provide fluid communication to the second reaction chamber and the reduction step is repeated there. The concentration of the resulting nitric oxide may be measured at this point.

It can be seen that the apparatus could thus be in the form of a loop in which the various oxidation and reduction cycles are conducted using the first and second chambers respectively. Thus in this embodiment the apparatus includes means for reintroducing the nitric oxide as a feedstock into the first chamber for further reaction. Thus, in one embodiment, the second reaction chamber includes means for conveying nitric oxide to the first chamber or to a further (third) chamber for reaction.

In an embodiment of the invention, the first and second reaction chambers do not need to be individual compartments. For instance, the nitric acid (in the presence of water) can be immobilized on or within a suitable substrate such as (open or porous) particles and the reducing agent is then also immobilized on or within a different substrate formed of similar or the same (open) particles. These particles can then be filled into a single column, either stacked in layers or in a partially or fully mixed arrangement (see FIG. 3 and the relevant description below). The column may be considered to be a composite column in this case as it contains all the materials necessary for both the oxidation and the reduction reactions to take place in a single reaction zone. In this case the individual amplification steps cannot be distinguished anymore. The gas sample passes through such the composite column and the concentration of NO and $NO_2$ is increased continuously as it does so, always dependent on there being sufficient reagents charged on to the column relative to the amount likely to be needed to progress both reactions.

In this embodiment, the situation is similar to the one found in chromatography (or column distillation), where theoretically a number of successive distribution steps occurs between the stationary and the mobile phase. In practice, however, these steps cannot be attributed to certain parts of the column. Therefore, in chromatography (also in column distillation) the "number of theoretical plates" is used, which describes, based on the outcome of the separation, the average number of theoretical distribution steps that have occurred. In a similar way, a number of theoretical amplification cycles could be determined for such a column by measuring the concentration of $NO/NO_2$ before and after passing through such a column. In the case of the analytical technique of the present invention, the method would require initial calibration with gas mixtures of known concentration. Since oxidation and reduction will occur simultaneously on the column, the exhausted gas mixture will contain NO as well as $NO_2$. Hence in a further embodiment, the composite column could be combined with a pure oxidation or reduction column prior to gas detection, depending on which gas is to be analysed (oxidation for $NO_2$ detection, reduction for NO detection).

One potential problem that might be expected in this composite arrangement might be due to the cross-reactivity of oxidizing (HNO3) and reducing agents, since they are in close proximity to each other. In fact, the individual particles may touch each other And therefore some loss of reagents would be expected to result due to direct reaction between them. However, this is mainly a problem during filling such a column. No significant effect will arise after equilibration of the column and removal of the gaseous reaction products. In a further embodiment, this problem is avoided by ensuring that during the filling/packing of the column open or porous particles that carry the active reagents preferably on their inner surface are used, such that the compounds would not come into contact with each other and cross reactions are avoided.

In an embodiment, the first chamber is a column. In another embodiment, the second chamber is a column. In either case, suitable columns include those used in gas chromatography. The column may be made from stainless steel.

In an embodiment, the apparatus includes a gas scrubbing unit. This is connected to the first chamber via suitable pipework and flow control valves as necessary.

It can be seen that a variety of means can be used for reintroducing the product of the reaction in one chamber as a feedstock into another chamber. This may be in the form of stainless steel pipework, for example such as that conventionally used in gas chromatography and the like. Valves and branches may be included in the flow path to ensure that any recirculated gas passes into the first vessel and does not escape from the system. The recirculated gas may or may not be passed through the scrubbing unit before entering the first vessel.

The apparatus is portable and highly flexible in use. In an embodiment, the reaction zone(s) is/are arranged so that the size of the apparatus including the reaction zone(s) is preferably not larger than $0.5 \times 0.5 \times 0.5$ m$^3$. More preferably the size is not larger than $0.3 \times 0.3 \times 0.3$ m$^3$. Even more preferably the size is not larger than $0.15 \times 0.15 \times 0.15$ m$^3$. The basic components that need to be encompassed in this apparatus comprise a means for gas injection, preferably a means to collect human breath, the reaction zone(s) for effecting amplification and an outlet to a detector and optionally a detector system. The detector system may, optionally, be a separate unit, that can easily be combined with the amplification unit. Preferably the amplification unit can be combined with a number of different detection systems and can be easily (e.g. with a single switch) adjusted to detection systems detecting either NO or $NO_2$. A detector based on a field effect transistor is ideal for this purpose.

In one embodiment the amplification system is a disposable i.e intended for single use. This guarantees a high reproducibility of the measurement. It may be used as a black box with an inlet for the gas sample and an outlet for connection to the detection system. It may be a cartridge for insertion into the detection system. It may also be reusable. In this case, it may be equipped with a regeneration unit, which provides reservoirs of $HNO_3$, water, and the reducing agent, to allow for re-loading of the oxidation and reduction columns with the respective species. The regeneration unit also provides a dispensing and control system to control the regeneration process.

The amplification system (in combination with a suitable detection system) may be equipped with an internal calibration system, which comprises a reservoir of one or more than one sources of NO (e.g. gas mixtures with different NO concentrations), a control system for the controlled release of NO from the reservoir(s) and for the correlation of the NO concentration in the calibration mixture with the correlated detector signal.

The columns will have a preferred inner diameter of 0.1-10 mm, more preferably 1-5 mm. The length of the columns used depends on their diameter. Very thin columns, such as chromatography-type columns can have an effective length of up to 10 meters or more, thicker columns will be significantly shorter.

Exhaled breath is a complicated mixture of as many as several hundreds of different components in different concentrations. The most common physical detection of NO is by electromagnetic absorption spectrometry in the infrared region. In the case of $NO_2$, the most common technique is by spectroscopy in the visible range of the electromagnetic spectrum. Ordinarily this can be disturbed or impeded by the absorption of other components in the sample. Even though other components may show absorption band maxima at different wavelengths there is often still significant absorption in the region of interest if these components are present in a sufficiently high concentration relative to the NO or $NO_2$.

Examples of molecules which cause unwanted absorption are water or carbon dioxide. Similar problems are commonly encountered in other detection methods (e.g. detection via field-effect transistor modification) as well. However, the present invention addresses this problem by increasing the relative concentration of the target species compared with the other components so that any undesired absorption due to interference from other components becomes insignificant.

The quality of the sensing method and its sensitivity is thus improved by increasing the analyte/"impurity" concentration ratio. The method of the invention selectively increases the concentration of the analyte i.e. the NO or $NO_2$, without changing the other concentrations.

In an embodiment, it is also possible to decrease the concentration of the disturbing component(s) by employing a system that removes selectively the interfering component(s) without changing the concentration of the analyte i.e. the NO or $NO_2$. This could, for instance, be achieved by a selective adsorption system that accumulates the analyte selectively prior to analysis.

Conversion of NO to $NO_2$ according to equation 1 above is a first order reaction in NO, which makes is relatively easy to control. The reaction is surface catalysed and has been shown to proceed on the surface of borosilicate glass, which is a commercial standard glass type. The reaction depends on the simultaneous presence of $HNO_3$ and water at the surface of the reaction system.

The reaction employed in the method of the present invention is a heterogeneous reaction in which NO from the gas phase is converted to $NO_2$ at a substrate and is then eventually again released to the gas phase. This method does thus not impose additional restrictions on existing sensor systems for gas phase analysis as the target species is in the gas phase and can easily be measured by conventional techniques. The method also has the advantage that it can tolerate relative humidities up to 100%.

The gain in output sensitivity is a factor of three based on the assumption that the sensitivity of NO and $NO_2$ detection are comparable. In reality the sensitivity gain can be smaller or bigger since detection methods for NO and $NO_2$ differ significantly and will depend on the detection method used. For instance, direct spectroscopic detection of gaseous NO is most selective in the IR region of the electromagnetic spectrum, whereas $NO_2$ can be detected rather selectively (and more economically) in the visible part of the spectrum, due to the brownish appearance of this radical species.

The amplification method of the present invention can be combined with a variety of final detection methods. Examples of suitable detection methods are discussed in a number of patent and non-patent documents and are therefore not discussed here in detail.

One known method of measuring nitric oxide concentrations in human breath is based on a semiconducting metal oxide sensor such as a tungsten trioxide thin film chemiresistive sensor element. The sensor element is highly sensitive to nitrogen dioxide ($NO_2$). Monitoring of NO is achieved via oxidation of the NO component in breath samples by an oxidising agent such as alumina supported potassium permanganate ($KMnO_4$) to $NO_2$. Such a sensor could easily be used to measure the concentration of $NO_2$ produced in the method of the present invention.

In our copending application relating to the use of a field effect transistor we describe a method for measuring nitric oxide at concentrations of ppb without the need for bulky trace gas analysis equipment of a conventional type. Such a detector would be well suited to measurement of the nitric oxide concentration produced by the amplification method of the present invention. The measurement can be achieved reliably and repeatably using an organic field effect transistor which is adapted to react selectively with nitric oxide in a gaseous sample to measure the concentration of nitric oxide present in the gas sample.

The field effect transistor is a multilayer heterostructure comprising an inorganic semiconductor substrate, an insulator layer covering the substrate layer, source and drain electrodes and an aryl amine semiconductor layer disposed on top of the insulating layer so as to at least provide an uninterrupted layer between the source and drain electrodes. A known potential difference is applied to the inorganic semiconductor layer and the layer of organic semiconductor is exposed to a gaseous sample. The characteristics of the source and drain electrodes are then measured. This method works by differential measurement of the response of the threshold voltage or change in drain current at a given gate bias (voltage) which can be correlated with a nitric oxide concentration.

This gate bias is the potential difference applied to the inorganic semiconductor layer. The detector is calibrated to determine the appropriate threshold voltage or drain current at a given gate bias in the absence of nitric oxide and also at various levels of nitric oxide concentration. The detector could be calibrated using a number of different gate bias values, for each bias value measuring a range of source and/or drain characteristics a different known nitric oxide concentration levels. In this way, calibration can be achieved for a range of bias values and concentrations thereby improving the accuracy of the detector output.

For further amplification of the analyte concentration in the method of the present invention, it is possible to use a multitude of amplification steps which can be combined as discussed above.

A cyclic amplification process, however, requires reduction or decomposition at higher temperatures of $NO_2$ back to NO, before a new cycle can be started. Since $NO_2$ is a strong oxidant, a variety of reducing agents may be used to achieve this reduction reaction. The stoichiometry of the thermal decomposition reaction is as set out in equation 4:

$$2NO_2 \rightarrow 2NO + O_2 \quad (4)$$

The reduction reaction can be very selective. For example, aromatic alcohols are selectively reduced to the corresponding aldehydes (equation 5):

$$RCH_2OH + NO_2 \rightarrow RCHO + NO + H_2O \quad (5)$$

This reaction is well known from alcohol breath analysis used in traffic control. Other effective reducing agents are disubstituted sulfides or trialkyl or triaryl phosphines, which are reduced selectively to the corresponding sulfoxides (equation 6):

$$R_2S + NO_2 \rightarrow R_2SO + NO \quad (6)$$

or phosphine oxides (equation 7), respectively:

$$R_3P + NO_2 \rightarrow R_3PO + NO \quad (7).$$

Application of the amplification system in exhaled breath analysis can be disturbed by the presence of other nitrogen compounds, which upon reaction with nitric acid are a potential source of nitrogen oxides, or by oxidizable components in general. The most important compound is ammonia, which can react vigorously with the offered $HNO_3$ to form ammonium nitrate, which in turn can further decompose or react to nitrogen oxides, such as $N_2O_3$, $NO_2$, or NO. As a consequence, a too high NO content could falsely be detected.

Basic nitrogen gasses should thus be removed from the analysis mixture prior to amplification. Most easily, this can be achieved by passing the gas mixture through a suitable chemical scrubbing unit to remove some or all of the unwanted components. This may be for example an acidic or neutral column through which the sample gas is initially passed before the amplification process. The scrubbing unit should have a sufficient capacity to adsorb all basic components. Examples of such columns are acidic ion exchange columns, (these can be based on sulfonic acid functionalised carrier materials, such as silica or other equivalent arrangements). Unmodified silica, however, could already be sufficiently effective to remove strongly basic ammonia completely. Control and monitoring of any side reactions can further be gained by careful blank and control measurements.

The amplification system for NO detection can be realized in variety of column designs. An important feature is the use of a chemically neutral or mildly acidic material as the substrate with a the capability to bind nitric acid and water reversibly by e.g. hydrogen bonding. The substrate material should be at least mildly hydrophilic. Ideal materials are borosilicate glass or silica. Hydrophilic or surface-hydrophilized polymers or polymers bearing surface functionalities suitable to reversibly bind water and nitric acid molecules without undergoing chemical change may also be used as well. Some other materials such as $\alpha$-$Al_2O_3$, $TiO_2$, $\gamma$-$Fe_2O_3$, CaO, and MgO may also be used but these need careful use since there is potentially the issue of adsorption of nitric acid due to chemical reaction of the $HNO_3$ with the metal oxide.

It is preferable that the substrate is in the form of an aggregate of loose particles and contains particles of small sizes, preferably of sub-millimetre size. More preferably particle sizes are 1-1000 μm and even more preferably particle sizes are 20-200 μm. This is advantageous due to the high surface-to-volume ratio and the consequent relatively large active surface area.

The present invention will now be described by reference to the following figures in which.

Figures 1A, 1B, 1C:
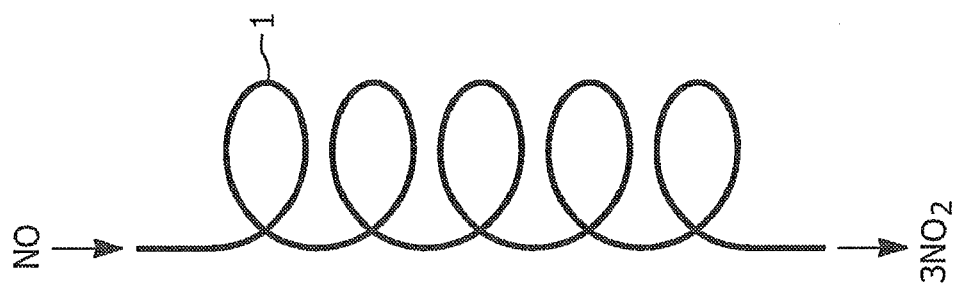
FIG. 1 shows three example column designs.

FIG. 1a) shows a column 1 which is based on thin commercial gas capillaries such as those used for example in gas chromatographic analysis systems. Such columns are easy to manufacture from standard borosilicate glass capillaries by pulling at high temperature. They provide a large inner surface, to which nitric acid can easily be deposited by passing $HNO_3$ (alternatively $NO_2$ or $N_2O_5+H_2O+O_2$) through the column. The use of dry $HNO_3$ gas is advantageous. The inner surface may have to be treated chemically to render it sufficient hydrophilic to allow effective binding of the stationary phase.

FIG. 1b) shows a short and wide column 2 filled with a substrate 3. For example this may be glass spheres of various shapes, which provide a sufficiently large surface for the heterogeneous reaction. The glass spheres can, for instance, be loaded with concentrated nitric acid solution or via the gas phase.

FIG. 1c) shows a similar column 4 to that described in FIG. 1b), but in this case is filled with a substrate 5 having a much smaller particle size. Suitable substrates include silica (e.g. silica gel microspheres with a diameter of a few micrometers). The smaller particle size allows for a higher surface density per column volume compared to that in FIG. 1b). Loading with $HNO_3$ can be done either via the gas phase or via solution exposure. The same types of columns can be used in the reduction reaction step, in which $NO_2$ is reduced back to NO. They are either filled with an inert carrier material, the surface of which is modified with a thin film of the reducing agent (held on the support in the columns of FIGS. 1a-1c). Alternatively they can be filled with the neat reducing agent, provided the column remains sufficiently open (porous) for gas transport.

Figure 2:
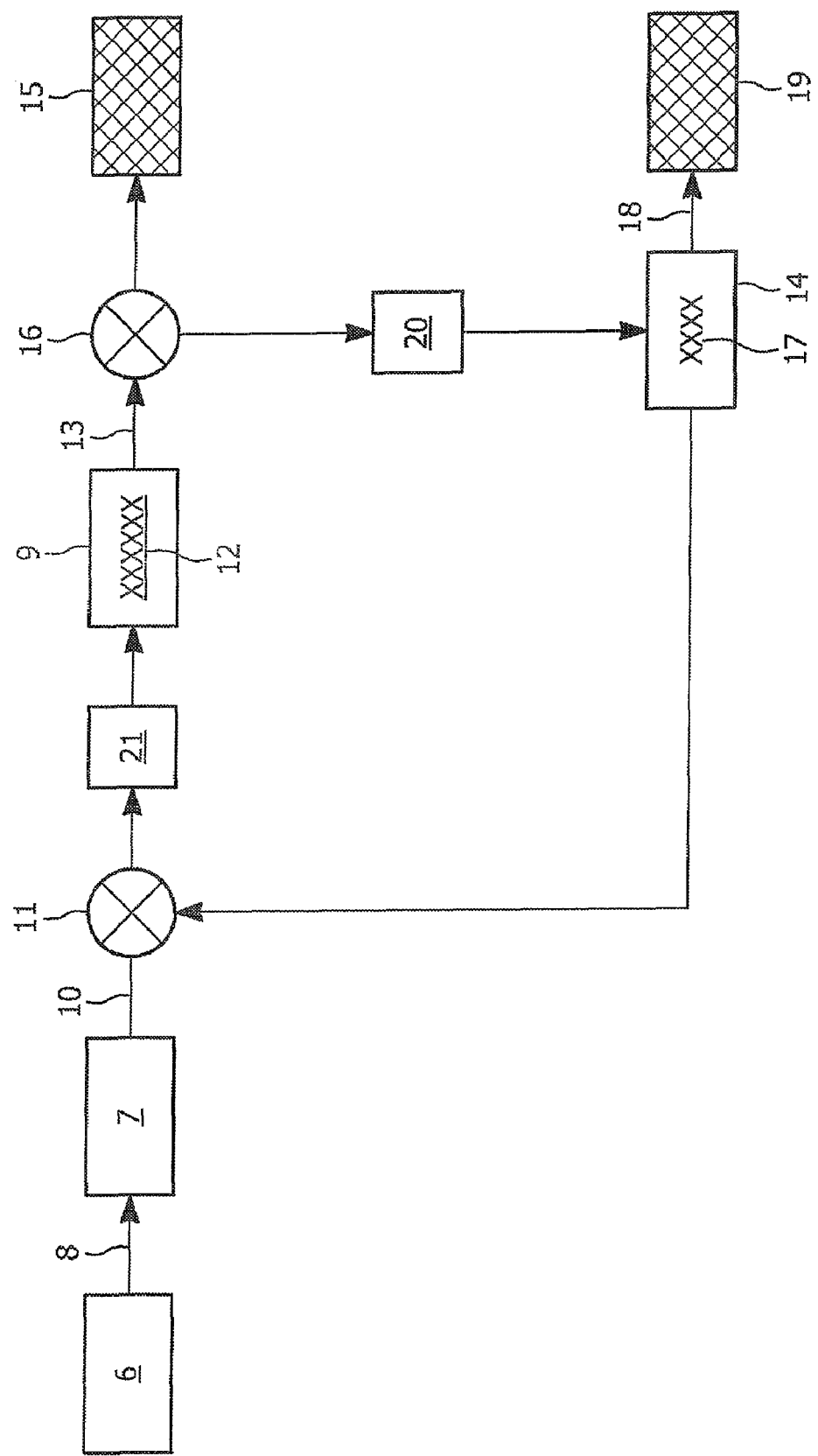
FIG. 2 shows a schematic diagram of a process according to the first aspect of the invention.
Figure 3D:
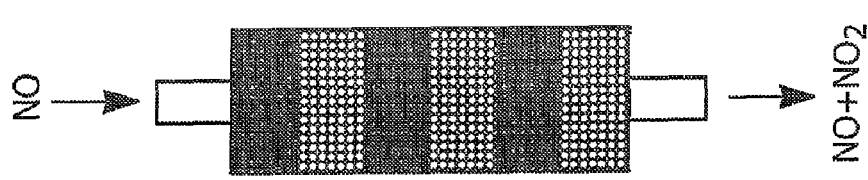
FIG. 3 shows a column according to the second aspect of the invention.
Figure 3C:
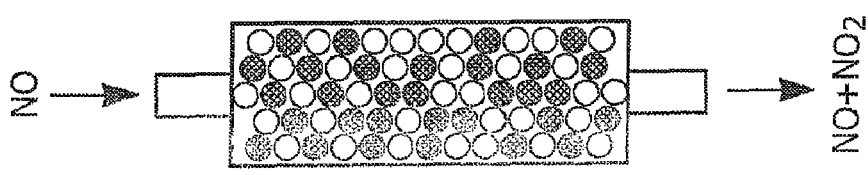
Figure 3B:
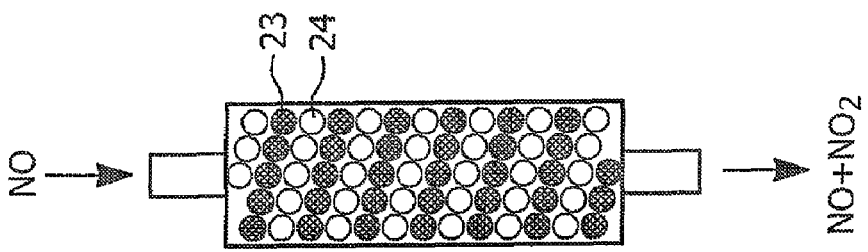
Figure 3A:
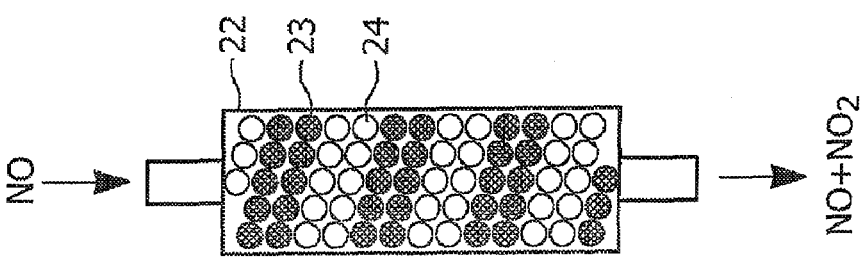

FIG. 2 shows a schematic diagram of a process according to the first aspect of the invention in which a number of oxidation and reduction step may be performed sequentially in a cyclic process. A gas sample 6 of known volume containing nitric oxide is collected and the temperature and pressure are noted. The sample is fed to the optional scrubber 7 by means of suitable pipework 8. The scrubber 7 is in fluid communication with a reaction chamber 9 by suitable pipework 10 and optional valve(s) 11 which are present as needed. Reaction chamber 9 contains a substrate 12 which is able to provide a source of nitric acid and water. The nitrogen dioxide produced by chemical reaction is fed from the chamber 9 via suitable pipework 13 either to a second reaction chamber 14 (when present) or to a detector 15. A valve 16 (present as necessary) controls the flow from chamber 9. When the nitrogen dioxide is fed to the second reaction chamber 14 it reacts with a reducing agent 17 which may or may not be supported on a substrate. The nitric oxide produced in this reaction is then fed via suitable pipework 18 either to a detector 19 or back to the first reaction chamber 9 for further reaction. Counters 20 and 21 log the number of times material is passed through the chambers 9 and 14 respectively to allow calculation of the initial concentration of nitric oxide based on the measured value of gas concentration. The cycles may be repeated a number of times as desired before detection of the gaseous product takes place and detection may occur either following an oxidation step or a reduction step.

FIG. 3 shows a column according to the second aspect of the invention. In this case the column 22 may contain the first 23 and second 24 substrates arranged in layers (FIGS. 3a, 3b, and 3d) or intimately mixed (FIG. 3c).

The invention claimed is:

1. A method of determining the concentration of nitric oxide in a gaseous sample, wherein the method comprises the following steps:
    a) collecting a gaseous sample containing nitric oxide,
    b) exposing the sample to a first substrate to which nitric acid is bound in the presence of water to form nitrogen dioxide by reaction with the nitric oxide,
    c) exposing the nitrogen dioxide to a second substrate (17) which is associated with a reducing agent so as to form amplified nitric oxide from any nitrogen dioxide present, and
    d) determining the concentration of nitric oxide in the gaseous sample from the amplified nitric oxide-produced in step,
    wherein the first and second substrates are comprised in a same substrate.

2. The method according to claim 1, further comprising:
    performing in turn one or more sequential exposing steps b) and c) on the gaseous sample resulting in amplified nitric oxide and then measuring the concentration of the resulting amplified nitric oxide or measuring the concentration of the resulting nitrogen dioxide.

3. The method according to claim 1, wherein the concentration of nitric oxide is determined by spectroscopy or gas chromatographic techniques.

4. The method according to claim 1, further comprising between steps a) and b) the step of:
    passing the sample through at least one chemical scrubbing unit.

5. The method according to claim 4, wherein the chemical scrubbing unit is an acidic or neutral column.

6. An apparatus for measuring the concentration of nitric oxide in a gaseous sample, the apparatus including the following components arranged in fluid communication:
    a vessel for collecting a gaseous sample containing nitric oxide;
    a reaction chamber in fluid communication with the vessel containing a first substrate whose surface is able to provide a source of nitric acid and water enabling the formation of nitrogen dioxide after exposition of the sample to the first substrate;
    a second substrate, the surface of which includes a reducing agent which forms amplified nitric oxide once in contact with the nitrogen dioxide; and,
    means for determining the concentration of the nitric oxide from the amplified nitric oxide,
    wherein the first and second substrates are intimately mixed.

7. The apparatus according to claim 6, wherein the first and second substrates are present as separate layers in the reaction chamber.

8. An apparatus for measuring the concentration of nitric oxide in a gaseous sample, the apparatus including the following components arranged in fluid communication:
    a vessel for collecting a gaseous sample containing nitric oxide;
    a reaction chamber in fluid communication with the vessel, the reaction chamber containing a first substrate, the first substrate being provided with a first substrate surface having a source of nitric acid and water enabling the formation of nitrogen dioxide after exposition of the sample to the first substrate and containing a second substrate, a second substrate surface of the second substrate including a reducing agent capable of forming amplified nitric oxide once in contact with the nitrogen dioxide; and,
    means for determining the concentration of the nitric oxide from the nitrogen dioxide,
    wherein the first and second substrates are comprised in a column, and
    wherein the first and second substrates are intimately mixed.

9. The apparatus according to claim 8, wherein further comprising:

a chemical scrubbing unit in fluid communications between the vessel and the reaction chamber.

10. The apparatus according to claim 9, wherein the chemical scrubbing unit is an acidic or neutral column.

11. The apparatus according to claim 8, wherein the first and second substrates are arranged in layers.

12. The apparatus according to claim 6, further comprising:

a fluid connection from and back to the reaction chamber via a valve(s) and a counter.

13. The apparatus according to claim 8, wherein further comprising:

a fluid connection between the reaction chamber and second reaction chamber via valve and counter.

* * * * *